United States Patent [19]

Zupancic et al.

[11] Patent Number: 5,085,886
[45] Date of Patent: Feb. 4, 1992

[54] PHOTODEFINABLE INTERLEVEL DIELECTRICS

[75] Inventors: Joseph J. Zupancic, Bensenville, Ill.; Daniel C. Blazej, Annandale; Howard A. Fraenkel, Lebanon, both of N.J.

[73] Assignee: Allied-Signal Inc., Morristown, N.J.

[21] Appl. No.: 630,107

[22] Filed: Dec. 19, 1990

[51] Int. Cl.⁵ .................................. B05D 3/06
[52] U.S. Cl. ............................ 427/43.1; 156/655; 156/659.1; 427/272; 427/379; 428/457; 525/534; 528/205
[58] Field of Search .................... 156/655, 659.1; 427/43.1, 272, 379; 428/457; 525/534; 528/205

[56] References Cited

U.S. PATENT DOCUMENTS 4,824,920  4/1989  Zupancic et al. .................. 525/534
4,908,096  3/1990  Zupancic ...................... 427/43.1 X Primary Examiner—Michael Lusignan
Attorney, Agent, or Firm—Harold N. Wells; Gerhard H. Fuchs; Mary Jo Boldingh

[57] ABSTRACT

A predetermined pattern of a dielectric polymer is formed on a substrate from a prepolymer which is an ether of the reaction product of a dicyclopentadiene and a phenol.

11 Claims, No Drawings

PHOTODEFINABLE INTERLEVEL DIELECTRICS

U.S. Government has rights in this invention under U.S. Air Force Contract F33615-89-C-5603

PRIOR ART

This invention relates to materials used to provide isolation of conductive layers in microelectronic circuitry. In particular, it relates to polymeric materials which can be photopolymerized so that dielectric layers can be formed where desired in multilayer structures. Such layers must be excellent insulators, have good chemical resistance and, of course, must adhere to the substrate on which they are placed.

Polyimides have been used for such dielectrics since they have superior temperature and chemical resistance compared to many other polymers. Literature and patents disclosing of the use of polyimides are extensively discussed in U.S. Pat. No. 4,908,096 by one of the present inventors and incorporated herein by reference. The disadvantages of the polyimides are discussed, namely, that they release large amounts of volatiles during curing, absorb moisture, have poor adhesion, and have a relatively high coefficient of expansion. The patent discloses and claims the use of other polymers as interlevel dielectrics having improved properties, namely, vinyl benzyl or alkyl ethers of the condensation products of dialdehydes and phenols.

The present invention relates to other polymers which have been found to provide useful interlevel dielectrics.

In U.S. Pat. No. 4,824,920 one of the present inventors has disclosed thermosetting resins which are vinyl-benzyl ethers of the reaction product of a dicyclopentadiene with a phenol and which have application to making laminated boards for electronic applications. The patent is incorporated by reference herein. Such resins have been found to be useful as precursors for polymers for interlevel dielectrics, as will be seen in the discussion below.

SUMMARY OF THE INVENTION

This invention comprises a method of forming a predetermined pattern from a polymer on a substrate and the thus-created dielectric layers which may be used in an electronic interconnect structure.

Such patterns are created by coating onto the substrate a prepolymer and then irradiating the exposed portions of a masking pattern to render the prepolymer insoluble, then selectively dissolving the non-irradiated masked portions of the coating leaving the insoluble irradiated prepolymer, and curing the irradiated prepolymer to form an infusible glassy solid in the predetermined pattern.

The prepolymer is an ether of the reaction product of a dicyclopentadiene with a phenol, the reaction product having the formula

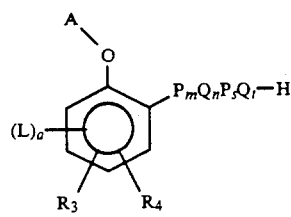

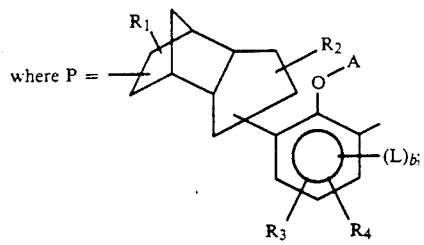

where P =

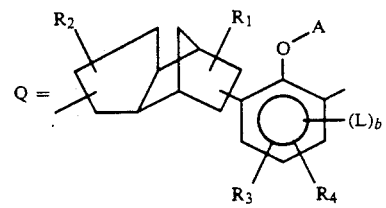

Q = with $R_1$, $R_2$ = H or alkyl of 1-10 carbon atoms;
$R_3$ = methyl;
$R_4$ = H;
A = H

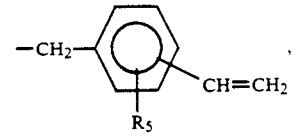

an alkyl moiety containing 1 to 10 carbon atoms, a cycloalkyl moiety having 5 to 10 carbon atoms, or benzyl, subject to the constraint that at least 50% of all A's are the vinyl benzyl moiety;
L = Br or Cl;
a = 0, 1, or 2;
b = 0 or 1;
m, n, s, and t are 0 or an integer, and $m+n+s+t=z$ is an integer from 1-10; and
$R_5$ = H, an alkyl moiety of 1-10 carbon atoms, a halogen or alkoxy moiety, or a monovalent aromatic radical.

In a preferred embodiment, 70% of A's are vinyl benzyl and the remaining A's are propyl.

DESCRIPTION OF THE PREFERRED EMBODIMENTS

Polymeric Resins

In U.S. Pat. No. 4,824,920, one of the present inventors disclosed the preparation and use of the vinylbenzyl ethers of the reaction product of a dicyclopentadiene with a phenol and their use in composites, especially laminated boards for electronic uses. It has now found that these compositions can be used as interlevel dielectrics, where they have the advantages of low water absorption, low dielectric constant, low coefficient of thermal expansion, high glass transition temperature, high thermal stability, high solids coating concentrations, photochemical curability, thermal curability, and little or no volatiles generated during the curing process.

The prepolymers used in forming a pattern have the formula

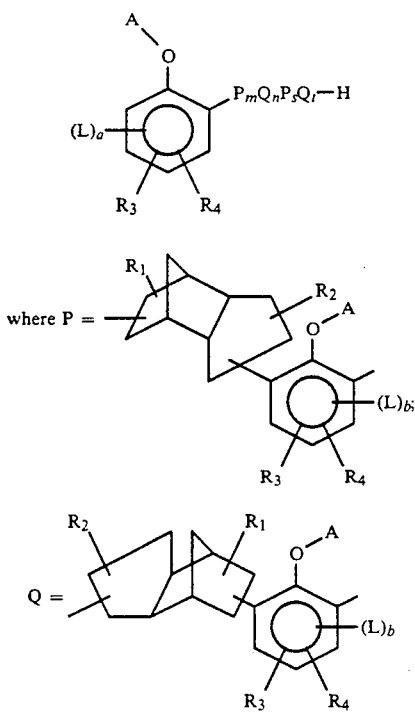

with $R_1$, $R_2 = H$ or alkyl of 1-10 carbon atoms;
$R_3$ = methyl;
$R_4 = H$;
$A = H$

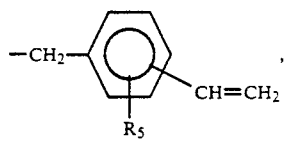

an alkyl moiety containing 1 to 10 carbon atoms, a cycloalkyl moiety having 5 to 10 carbon atoms, or benzyl, subject to the constraint that at least 50% of all A's are the vinyl benzyl moiety;
L = Br or Cl;
a = 0, 1, or 2;
b = 0 or 1;
m, n, s, and t are 0 or an integer, and $m+n+s+t = z$ is an integer from 1-10; and
$R_5 = H$, an alkyl moiety of 1-10 carbon atoms, a halogen or alkoxy moiety, or a monovalent aromatic radical.

The dicyclopentadiene portion can be substituted in either ring. $R_1$ and $R_2$ usually are hydrogen, that is, an unsubstituted dicyclopentadiene is preferred in the practice of this invention but each of $R_1$ and $R_2$ can be an alkyl group, preferably a primary alkyl group, containing up to about 10 carbon atoms. The lower alkyl groups, such as methyl, ethyl, propyl, and butyl, are especially preferred where the dicyclopentadiene is substituted. Substitution can be at any position of the dicyclopentadiene ring system but it is preferred that $R_1$ be at a carbon of the 5-member ring not bonded to the aryl group, and that $R_2$ is at the bridge or bridgehead carbon of the bicyclic ring portion.

The phenolic termini of our resins as well as the phenolic portion of P or Q may be substituted by a C methyl or a halogen atom. For the condensation with dicyclopentadiene mixtures of such phenols also may be used. The methyl group is at a position meta or para to the position bearing the oxygen atom. A parasubstituted phenol is preferred in the practice of this invention because it tends to afford an amorphous resin, which is a beneficial feature, and renders the resin susceptible to photochemical curing.

The basic resins also can be readily modified to be flame retardant by incorporating halogen atoms into the aromatic rings. Thus, L may be a halogen atom, especially bromine, and where the aromatic ring is halogenated a is 1 or 2 and b is 0 or 1. Polyhalogenated materials are desired as flame retardants, which means that a and b are recommended to be maximized. Where the aromatic rings are not halogen substituted then both a and b are 0.

The fragments P and Q are subunits of the adduct. Where the adduct is an oligomer it may be a head-to-head, head-to-tail, or completely or partially random arrangement. Where oligomers are formed they are of relatively low molecular weight. The variables m, n, s, and t each are integers such that z, where z equals $m + n + s + t$, is an integer from 1 to 10, and usually is up to about 5, with z being 3 or 4 preferred in the practice of our invention.

The phenolic hydroxyls in the adduct are capped so as to be converted to ethers. At least 80% of the phenolic groups are so capped, and it is desirable that at least 90%, and even more desirable that at least 95%, of the phenolic groups be capped. Stated differently, in the formula above less than about 20% of the A moieties are hydrogen, and desirably less than 10%, even more desirably less than 5%, are hydrogen.

The best case results where the ether portion, A, is a vinylbenzyl moiety, that is, of the structure

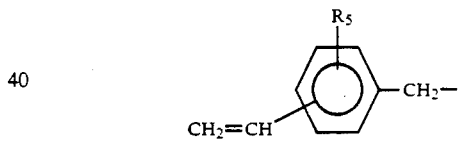

where the vinyl group is either meta or para to the $CH_2$, where $R_5$ is hydrogen, and which usually is a mixture of the meta- and para-isomers. $R_5$ is a chemically inert substituent selected from the group consisting of hydrogen, alkyl moieties containing from 1 to about 10 carbon atoms, the halogens, alkoxy moieties containing from 1 to about 10 carbon atoms, and monovalent radicals whose parent is an aromatic hydrocarbon. However desirable it may be to have all the phenolic hydroxyls end-capped with vinylbenzyl moieties, there is a decided cost advantage when fewer than all of the other groups are vinylbenzyl usually at the expense of a somewhat lower dielectric constant. In our invention it is required that at least 50% of the A moieties different from hydrogen be a vinylbenzyl moiety, but a product with better performance characteristics results when from 70 to 100% of the ether groups are vinylbenzyl, and the best product results when 95 to 100% of such groups are vinylbenzyl. However, for many applications less than complete end-capping with vinyl benzyl groups is acceptable, but all of the hydroxyl groups should be capped.

In those cases where less than all of the ether groups are vinylbenzyl, then we are partial to resins where A is an alkyl group containing from 1 to 10 carbons, a cycloalkyl group having 5 to 10 carbons, or a benzyl group.

Where A is an alkyl group, the primary alkyl groups are given priority, especially the primary lower alkyl groups containing from 1 to 4 carbon atoms. Thus, the most desirable alkyl groups consist of methyl, ethyl, 1-propyl, 1-butyl, and 2-methyl-1-propyl. Other alkyl groups are represented by 1pentyl, 1-hexyl, 1-heptyl, 1-octyl, 1-nonyl, 1-decyl, 2-methyl-1-butyl, 3-methyl-1-butyl, 2,3-dimethyl-1-butyl, 3,3-dimethyl-1-butyl, 2-methyl-1-pentyl, and so forth. However, it is to be emphasized that a benzyl group also operates quite satisfactorily in the practice of our invention. The most common cycloalkyl groups used in our invention are 5- and 6-membered cycloalkanes, unsubstituted or alkyl substituted so as to contain 5 to 10 carbon atoms. Examples are cyclopentyl, cyclohexyl, methylcyclopentyl, dimethylcyclopentyl, ethylcyclopentyl, propylcyclopentyl, butylcyclopentyl, pentylcyclopentyl, ethylmethylcyclopentyl, methylpropylcyclopentyl, butylmethylcyclopentyl, methylcyclohexyl, dimethylcyclohexyl, ethylcyclohexyl, propylcyclohexyl, butylcyclohexyl, and so forth. The 1-propyl group is an especially desirable alternative to the vinylbenzyl moiety, and resins where less than 5% of the A groups are hydrogen with the remainder being vinylbenzyl or 1-propyl in a ratio from 1.1:1 to about 6:1 are highly recommended. In a preferred embodiment, A is at least 70% vinyl benzyl and the remaining A's are propyl. The use of a mixture tends to promote formation of an amorphous resin which is desirable both in increasing the solubility of the resin in solution, in promoting good film-forming qualities, and in providing a stable, non-flaking coating. A desirable mixture of resins is one which consists of from about 5 to about 20% by weight of a resin where $z = 1$, about 10 to about 30% with $z = 2$, about 5 to about 30% with $z = 3$, about 5 to about 30% with $z = 4$, and about 5 to about 30% with $z = 5-10$.

The appended vinyl groups are readily crosslinked in a curing step effected by thermal, chemical, or radiative means. Thermal curing is generally done in the temperature range between about 100° and about 300° C., and in practice at a temperature between about 150° and about 200° C. for 0.5-5 hours with post curing at about 180°-300° C. for about 0.5-24 hours. Curing also may be brought about using a free radical initiator, such as azo-bis-isobutylronitrile, benzoyl peroxide, di-t-butyl peroxide, etc. Curing may be effected as well as irradiation, especially by visible and ultraviolet light in the presence of a suitable photoinitiator or sensitizer. Whether thermal, chemical, or photochemical curing is performed, the resin becomes extensively crosslinked and sets to an infusible, insoluble glassy solid.

The resins of this invention may be prepared by an convenient method known in the art. However, they are most readily prepared by reacting a vinylbenzyl halide with the dicyclopentadiene-phenol adduct in a basic solution. Generally a mixture of the meta- and para-isomers of vinylbenzyl chloride are used, although the bromide and, to a lesser extent, the iodide also may be used. The reaction may be conveniently performed in an alcoholic potassium hydroxide solution, often containing acetone, N-methylpyrrolidone, or some other organic cosolvent, at the reflux temperature. Where some of A are alkyl, cycloalkyl, or benzyl moieties there may be prepared by reacting a suitable alkyl, cycloalkyl, or benzyl halide with a partially vinylbenzyl end-capped adduct, or by reacting the uncapped adduct with a mixture of halides.

Photodefinable Applications

The oligomers may be used as a passivant, as an interlevel dielectric, as a means of providing device deep dielectric isolation (insulator isolating trenches), as a high temperature solder mask, a photoresist, etc. Although much of what follows describes its use primarily as an interlevel dielectric, the skilled worker will recognize from this description how to use the materials of this invention in other applications as well.

The oligomers are applied as a coating to a suitable substrate. For the most part the substrates used will be a silicon wafer, a silicon chip of an integrated circuit, a printed circuit board or a ceramic substrate. The photosensitive oligomers may be applied by spin coating, spray coating, by use of a doctor knife, or any other conventional techniques known in the art to obtain a uniform coating. Where the viscosity is too high, a solution of the resin in a suitable solvent may be used. The oligomers are soluble in a broad class of solvents including polar aprotic solvents, aromatic hydrocarbons, halogenated hydrocarbons, ketones, ester, and so forth. Examples of solvent which may be employed in the practice of our invention include dimethylformamide (DMF), hexamethylphosphoramide (HMPA), N-methylacetamide (NMAc), dimethylsulfoxide (DMSO), N-methylpyrrolidone (NMP), benzene, toluene, xylene, dichloromethane, chloroform, carbon tetrachloride, chlorobenzene, tetrachloroethane, tetrachloroethylene, trichloroethane, gamma-butyrolactone, methyl ethyl ketone, diethyl ketone, hexanone, heptanone, octanone, methyl acetate, ethyl acetate, methoxy ethanol, ethoxy ethanol, and so forth. The solvent should be unreactive with both the substrate and the photosensitive oligomers and able to dissolve the resins to provide at least about a 10 weight-volume percent solution. Since the solvent is typically removed prior to further processing, it is also preferable that as low boiling a solvent as possible be used consistent with the foregoing considerations.

Although the oligomers may be photopolymerized directly, a photosensitizer or photoinitiator may be used and may be useful to decrease irradiation time. Where a photosensitizer is used it will be added with the oligomers at the coating stage and will be present in an amount from about 0.001 to about 5.0 weight percent relative to the oligomerics. Examples of photosensitizers or photoinitiators which may be successively used in the practice of this invention include such materials as benzophenone, 4,4'-bis(dimethylamino)benzophenone, xanthone, acetophenone, 4-trifluoromethyl-acetophenone, triphenylene, thioxanthone, anthraquinone, 4-phenylbenzophenone, naphthalene, 2-acetonaphthalene, 1-acetonaphthalene, chrysene, anthracene, 9,10-dichloroanthracene, pyrene, triphenylene, 1-fluoronaphthalene, 1-chloronaphthalene, 1-bromonaphthalene, 1-iodonaphthalene, 1,3-dicyanobenzene, dimethyl isophthalate, diethyl isophthalate, methyl 3-cyano-benzoate, ethyl 3-cyano-benzoate, phenyl 3-cyano-benzoate, 2,2-dimethoxyacetophenone, 2,2-diethoxyacetophenone, 2,2'-dimethoxy-2-phenylacetophenone, 2,2'-diethoxy-2-phenylacetophenone, benzoin methyl ether, and 1-phenyl-1,2-propanedione-2-O-benzoyloxime. Preferred sensitizers include benzophenone, 4,4'-bis(dimethylamino)benzophenone, 1,3-dicyanobenzene, dimethyl isophthalate, diethyl isophthalate, methyl 3-cyano-benzoate, and phenyl 3-cyano-benzoate.

Where the photosensitive oligomers have been applied as a solution to the substrate the solvent used must be removed prior to irradiation. Consequently, it is conventional to heat the coated substrate for a time sufficient to remove essentially all of the solvent present, if any, prior to irradiation, a stage known as the "softbake." It is for this reason that the use of a low boiling solvent is preferred. It is acceptable to use enough heat to provide a semicured coating, especially since the oligomers may begin to cure at temperatures as low as about 110° C. The softbake can be carried out in vacuum, under an inert atmosphere (e.g., nitrogen, helium, argon, etc.) or in air.

A mask containing the desired pattern or image is placed on or adjacent to the coated substrate and the oligomeric coating is then irradiated through the mask by x-ray, electron beam, ion beam, ultraviolet, or visible radiation. For reasons of economy and ease of fabrication it is preferred to use radiation in the range from about 200 to about 800 nanometers. Since lower wave length radiation tends to afford better resolution, irradiation in the 200–500 nm range is preferred. With this treatment the irradiated portion of the coating becomes crosslinked so that the photocrosslinked oligomer is rather insoluble in the same solvent in which the original photosensitive oligomers remain quite soluble.

Irradiation may be done in either the presence or absence of oxygen. Exposure time necessary for adequate photocrosslinking to afford the differential solubility characteristic sought depends upon the wavelength of the light used, its intensity, the presence or absence of a photosensitizer or photoinitiator, and so forth, with a variation from a few seconds up through several minutes. For production purposes the shorter exposure times are highly preferred. One desirable characteristic of the photosensitive oligomers of this invention is that they photochemically crosslink throughout the thickness of the film, and therefore the pattern shows minimal undercutting upon development.

The selective pattern appears upon development with the solvent. As mentioned above, upon irradiation the photosensitive oligomeric resin becomes extensively crosslinked with a subsequent large differential solubility between the crosslinked, or irradiated, and non-crosslinked, or non-irradiated, portions of the oligomers. The solvents used in the development are in general the same ones used in preparing a solution of the oligomers for coating purposes. Thus, classes of solvents include aprotic solvents, aromatic hydrocarbons, halogenated hydrocarbons, ketones, esters, the Carbitols, and mixtures thereof.

Upon development selective patterns appear where the elevated portions correspond to the photochemically crosslinked oligomers. These relief structures are then thermally cured to afford a highly crosslinked, infusible, glassy solid highly resistant to elevated temperatures, chemical degradation, ion transport, and which serves as an effective protective layer and dielectric insulator. Curing is attended by crosslinking of the vinyl groups and may be effected either thermally, chemically, or photochemically, with thermal curing preferred. Thermal curing is generally done in the temperature range between about 100° C. and about 300° C., and often is done in stages. So, for example, curing may first be effected at a temperature between about 150° C. and about 200° C. for 0.5–5 hours with postcuring at about 180° C.–300° C. for about 0.5–24 hours. Curing also may be brought about using a free radical initiator, such as azo-bis-isobutyronitrile, benzoyl peroxide, di-t-butylperioxide, and so on.

The oligomers of the invention have been found particularly useful in photodefinable applications since they may be coated as solutions with high solids levels and thus less solvent must be evaporated. Also, since no volatile by-products are generated during curing the shrinkage of the films is minimized.

MULTILAYER PROCESSING

The substrate (i.e., ceramic, alumina, silicon, printed wiring board, etc.) may be cleaned with conventional cleaning solvents (e.g., methylene chloride, chloroform, Genesolv ®, trichloroethylene, ethanol, methanol, sodium bisulfite, sodium sulfite, potassium sulfite, etc.) employing normal cleaning processes as known in the art. In addition, the substrate may contain circuitry already deposited upon it. The substrate may be utilized after the cleaning process or may be surface treated to promote adhesion between the substrate and the metals and/or polymer dielectric layer.

If used, an adhesion promoter between the substrate and the dielectric layer may be chosen from a range of surface silylating agents containing reactive groups capable of reacting with the polymers of the invention. Examples of surface silylating agents which can be employed are: vinylmethyldimethoxysilane, vinyltrimethoxysilane, vinylmethyldiethoxysilane, vinyltriethoxysilane, diethoxymethylvinylphenethylsilane, dimethoxymethylvinylphenethylsilane, triethoxyvinylphenethylsilane, trimethoxyvinylphenethylsilane, etc. Preferred silylating agents are vinylmethyldimethoxysilane, vinylmethyldiethoxysilane, di ethoxyme thylvinylphenethyl silane, and dimethoxymethylvinylphenethylsilane. The surface silylating agent would be applied to the substrate via dipping, spin coating, or other techniques from a 1 to 10% solution of the silylating agent dissolved in 85 to 98 wt.% of alcohol (e.g., methanol, ethanol, isopropanol, etc.) and 1 to 13 wt.% of water. The substrate is dipped in this solution for 15 seconds to 5 minutes, air dried for 1 minute to 5 hours, and then soft baked for 1 minute to 5 hours at 60° to 100° C. either in a convection oven, vacuum oven or hot plate.

The cleaned and/or surface treated substrate will be covered with a metal pattern before being covered with the dielectric layer of the invention. For example, a 500 to 1000 Å layer of chromium, 8000 to 20000 Å layer of copper and a 500 to 1000 Å layer of chromium may be sputtered onto the surface. Then, the metal layer is coated with a commercial photoresist and processed according to the recommended processing scheme utilizing a spin coat, soft bake, imaging, developing, and hard bake cycle. This exposes portions of the metal layer to be removed by etching to create the pattern. The metals are etched utilizing standard wet techniques, for example: The top chromium layer is etched with a 1 to 30 % hydrochloric acid solution activated with aluminum for 10 seconds to 5 minutes; the copper layer is etched with a sodium persulfate solution for 10 seconds to 10 minutes; the bottom chromium layer is etched with a 1 to 30 % hydrochloric acid solution activated with aluminum for 10 seconds to 5 minutes; and finally the etched substrate is washed with deionized water for 10 to 60 seconds. Then the remaining photoresist is stripped from the metal pattern as per the processing technique recommended for the photoresist. Finally the cleaned substrate is dried prior to the next processing step.

The dielectric layer is coated onto the substrate and its metal pattern and processed as follows: The prepolymer (e.g., 10 to 80 wt. %) solution in an appropriate solvent (toluene, NMP, DMF, etc.) is spin coated onto the substrate at a speed of 500 to 2500 rpm for 30 to 90 seconds; the prepolymer coated substrate is soft baked at a temperature of 25 to 60° C. for 15 minutes to 24 hours in a vacuum oven with or without a nitrogen bleed; the soft-baked coating is then imaged with a UV light source (220-320 nm range) for 15 seconds to 30 minutes employing a mask of desired design for vias and the like; the photocured polymer is then developed with an appropriate solvent system (e.g., toluene, toluene/hexane, toluene/ethanol, cyclohexane, etc.) at 25° to 35° C. with or without ultrasonics or via spraying for 15 to 120 seconds; the developed substrate can then be exposed to a stop or rinse bath or solvent spray based upon a solvent system miscible with the developing solvent but a poor solvent for the polymer system (for example hexane, pentane, ethanol, etc.) (optional step); the vias are then cleaned with a plasma or wet etch; and finally the dried substrate is hard baked in vacuum or under an inert atmosphere (nitrogen, argon, etc.) with a cure cycle including a ramp from 25° to 300 C. for 30 minutes to 2 hours, a hold at 300° C. for 1 hour and then a cool down from 300° to 25° C. with a 30 minute to 3 hour ramp.

The process is repeated as required in order to form an electronic interconnect structure of desired electrical and dielectric levels.

EXAMPLE 1

Synthesis of Styrene Terminated Para-Cresol Dicyclopentadiene (STPCDP (70VBz/30Pr))

200.0 grams of the para-cresol dicyclopentadiene (PCDP) from Borden Chemical ($Mn=520$, $Mw=1100$, dispersity of 2.12) was dissolved in 700 mL of N-methylpyrrolidinone (NMP) in a 2000 mL 3-neck round bottom flask equipped with mechanical stirrer, addition funnel, condenser, thermometer, nitrogen purge and Therm-O-Watch. To this reaction mixture was added 123.06 g (0.806 moles) of vinylbenzylchloride (60/40 para/meta isomer ratio) and 0.30 g of 2,6-di-tert-butyl-p-cresol (BHT). The reaction mixture was heated to 60° C. and 52.78 g (0.941 moles) of potassium hydroxide in 125 mL of methanol was added dropwise over a 30 minute interval. The reaction was maintained at 60° C. for 16 hrs with stirring under a nitrogen purge. To this reaction mixture was added 1.32 g (0.254 moles) of n-propylbromide and then 15.34 g (0.273 moles) of potassium hydroxide in 80 mL of methanol over a 1 hr.interval. The reaction was maintained at 60° C. for 3.5 hours and then allowed to cool to room temperature. The reaction mixture was then transferred to a separatory funnel, and 2.0 Liters of toluene added and then washed thrice with 1.0 Liters of water, dried over magnesium sulfate, filtered and concentrated under vacuum, yielding a red resinous product; $Mn=630$, $Mw=1200$, dispersity of 1.9.

EXAMPLE 2

Synthesis of Styrene Terminated Para-Cresol Dicyclopentadiene (STPCDP (70VBz/30Pr))

500.0 grams of the para-cresol dicyclopentadiene (PCDP) from Borden Chemical (Mn 520, $Mw=1100$, dispersity of 2.12) was dissolved in 1750 mL of N-methylpyrrolidinone (NMP) in a 5000 mL 3-neck round bottom flask equipped with mechanical stirrer, addition funnel, condenser, thermometer, nitrogen purge and Therm-O-Watch. To this reaction mixture was added 307.65 g (2.016 moles) of vinylbenzylchloride (60/40 para/meta isomer ratio) and 1.43 g of 2,6-di-tert-butyl-p-cresol (BHT). The reaction mixture was heated to 60° C. and 131.95 g (2.35 moles) of potassium hydroxide in 312 mL of methanol was added dropwise over a 6.0 hrs. interval The reaction was maintained at 60° C. for 16 hrs. with stirring under a nitrogen purge. To this reaction mixture was added 78.30 g (0.637 moles) of n-propylbromide, and then added 38.35 g (0.630 moles) of potassium hydroxide in 200 mL of methanol over a 20 minute interval. The reaction was maintained at 60 C for 3.5 hours and then allowed to cool to room temperature. The reaction mixture was then transferred to a separatory funnel, and 2.0 Liters of toluene added and then washed with 2.0 Liters of water, once with saturated sodium chloride solution, and finally washed with a saturated ammonium chloride solution, dried over magnesium sulfate, filtered and concentrated under vacuum, yielding a red resinous product; $Mn=500$, $Mw=960$, dispersity 1.9.

EXAMPLE 3

Synthesis of Styrene Terminated Para-Cresol Dicyclopentadiene (STPCDP (70VBz/30Pr))

324.0 grams (2.996 moles) of para-cresol was charged into a 1000 mL 3-neck round bottom flask equipped with mechanical stirrer, addition funnel, condenser, thermometer, Therm-O-Watch, and Nitrogen purge. The reaction flask is heated to 90° C. under nitrogen with stirring. To the melted p-cresol is added 6.0 mL (0.041 moles) of boron trifluoride etherate. To this reaction mixture was added 262.0 g (1.982 moles) of dicyclopentadiene over a 2.2 hour interval, the reaction was maintained at 90° C. for 1 hour with stirring; then the unreacted p-cresol was vacuum distilled from the reaction mixture. The para-cresol dicyclopentadiene (PCDP) resin was isolated by pouring into a stainless steel pan and allowing to cool to ambient temperature; $Mn=650$, $Mw=1500$, dispersity of 2.31.

207.2 grams of the para-cresol dicyclopentadiene (PCDP) from above was dissolved in 700 mL of N-methylpyrrolidinone (NMP) in a 2000 mL 3-neck round bottom flask equipped with mechanical stirrer, addition funnel, condenser, thermometer, nitrogen purge and Therm-O-Watch. To this reaction mixture was added 127.5 g (0.835 moles) of vinylbenzylchloride (60/40 para/meta isomer ratio) and 0.20 g of 2,6-di-tert-butyl-p-cresol (BHT). The reaction mixture was heated to 60° C. and 54.68 g (0.975 moles) of potassium hydroxide in 130 mL of methanol was added dropwise over a 2.0 hours interval. The reaction was maintained at 60° C. for 16 hrs with stirring under a nitrogen purge. To this reaction mixture was added 32.45 g (0.263 moles) of n-propylbromide, and then added 15.89 g (0.283 moles) of potassium hydroxide in 80 mL of methanol over an 1.33 hour interval. The reaction was maintained at 60° C. for 8 hours and then allowed to cool to room temperature. The reaction mixture was then transferred to a separatory funnel, and 1.5 Liters of toluene added and then washed thrice with 2.0 Liters of water, dried over magnesium sulfate, filtered and concentrated under vacuum, yielding a red resinous product; $Mn=770$, $Mw=1400$, dispersity of 1.82.

EXAMPLE 4

Synthesis of Styrene Terminated Para-Cresol Dicyclopentadiene (STPCDP (70VBz/30Pr))

500.0 grams of para-cresol dicyclopentadiene (PCDP) from Borden Chemical ($M_n$ 520, $M_w$ 1100, dispersity of 2.12) and 420 mL of ortho-dichlorobenzene was charged into a 2000 mL 3-neck round bottom flask equipped with mechanical stirrer, addition funnel, condenser, thermometer, Therm-O-Watch, and Nitrogen purge. The reaction mixture was heated to 60° C. under nitrogen with stirring; after complete dissolution of PCDP then 6.0 mL (0.041 moles) of boron trifluoride etherate was added. To this reaction mixture was added 71.12 g (0.538 moles) of dicyclopentadiene over a 1.1 hour interval, the reaction was maintained at 60° C. with stirring during the addition; then the reaction was heated to 150° C. for 4 hours. The ortho-dichlorobenzene and unreacted dicyclopentadiene was vacuum distilled from the reaction mixture. The para-cresol dicyclopentadiene (PCDP) resin was isolated by pouring into a stainless steel pan and allowing to cool to ambient temperature, yield 332.0 g; $M_n$=800, $M_w$=2500, dispersity of 3.12.

318.5 grams of the para-cresol dicyclopentadiene (PCDP) from above was dissolved in 1100 mL of N-methylpyrrolidinone (NMP) in a 2000 mL 3-neck round bottom flask equipped with mechanical stirrer, addition funnel, condenser, thermometer, nitrogen purge and Therm-O-Watch. To this reaction mixture was added 195.0 g (1.278 moles) of vinylbenzylchloride (60/40 para/meta isomer ratio) and 0.30 g of 2,6-di-tert-butyl-p-cresol (BHT). The reaction mixture Was heated to 60° C. and 84.05 g (1.498 moles) of potassium hydroxide in 200 mL of methanol was added dropwise over a 3 hour interval. The reaction was maintained at 60° C. for 16 hrs with stirring under a nitrogen purge. To this reaction mixture was added 49.88 g (0.406 moles) of n-propylbromide, and then 24.43 g (0.435 moles) of potassium hydroxide in 125 mL of methanol added over a 2 hour interval. The reaction was maintained at 60° C. for 4 hours and then allowed to cool to room temperature. The reaction mixture was then transferred to a separatory funnel, and 1.5 Liters of toluene added and then washed once with 4 Liters of water and twice with saturated sodium chloride solution, dried over magnesium sulfate, filtered and concentrated under vacuum, yielding a red resinous product; $M_n$=700, $M_w$=1600, dispersity of 2.3.

EXAMPLE 5

Synthesis of Styrene Terminated Para-Cresol Dicyclopentadiene (STPCDP (70VBz/30Pr))

324.0 grams (2.996 moles) of para-cresol was charged into a 1000 mL 4-neck resin kettle equipped with mechanical stirrer, addition funnel, condenser, thermometer, Therm-O-Watch, and Nitrogen purge. The reaction flask is heated to 90° C. under nitrogen with stirring. To the melted p-cresol is added 6.0 mL (0.041 moles) of boron trifluoride etherate. To this reaction mixture was added 288.2 g (2.180 moles) of dicyclopentadiene over a 1.5 hour interval, the reaction was maintained at 90° C. for 1 hour with stirring; then the unreacted p-cresol was vacuum distilled from the reaction mixture. The para-cresol dicyclopentadiene (PCDP) resin was isolated by pouring into a stainless steel pan and allowing to cool to ambient temperature, yield 456.0 g; $M_n$=720, $M_w$=1900, dispersity of 2.64.

436.0 grams of the para-cresol dicyclopentadiene (PCDP) from above was dissolved in 1200 mL of N-methylpyrrolidinone (NMP) in a 2000 mL 3-neck round bottom flask equipped with mechanical stirrer, addition funnel, condenser, thermometer, nitrogen purge and Therm-O-Watch. To this reaction mixture was added 269.0 g (1.763 moles) of vinylbenzylchloride (60/40 para/meta isomer ratio) and 0.45 g of 2,6-di-tert-butyl-p-cresol (BHT). The reaction mixture was heated to 60° C. and 106.0 g (1.890 moles) of potassium hydroxide in 250 mL of methanol was added dropwise over a 2.5 hour interval. The reaction was maintained at 60° C. for 16 hrs with stirring under a nitrogen purge. To this reaction mixture was added 02.0 g (0.829 moles) of n-propylbromide was added to the reaction mixture and heated with stirring under purge to 60° C. To this reaction mixture was then added 35.4 g (0.631 moles) of potassium hydroxide in 120 mL of methanol over a 1.5 hour interval. The reaction was maintained at 60° C. for 3 hours and then allowed to cool to room temperature The reaction mixture was then transferred to a separatory funnel, and 4 Liters of toluene added and then washed four times with 2.0 Liters of water and once with saturated sodium chloride solution, dried over sodium sulfate, filtered and concentrated under vacuum, yielding a red resinous product; $M_n$=780, $M_w$=1600, dispersity of 2.1.

EXAMPLE 6

Synthesis of Styrene Terminated Para-Cresol Dicyclopentadiene (STPCDP (70VBz/30Pr))

628.0 grams (5.807 moles) of para-cresol was charged into a 2000 mL 3-neck round bottom flask equipped with mechanical stirrer, addition funnel, condenser, thermometer, Therm-O-Watch, and Nitrogen purge. The reaction flask is heated to 90° C. under nitrogen with stirring. To the melted p-cresol is added 12.0 mL (0.082 moles) of boron trifluoride etherate. To this reaction mixture was added 524.0 g (3.963 moles) of dicyclopentadiene over a 3.0 hour interval, the reaction was maintained at 90° C. for 1 hour with stirring; then the unreacted p-cresol was vacuum distilled from the reaction mixture. The para-cresol dicyclopentadiene (PCDP) resin was isolated by pouring into a stainless steel pan and allowing to cool to ambient temperature, yielding 612.2 g of resin; $M_n$ =990, $M_w$=2900, dispersity of 2.93.

591.2 grams of the para-cresol dicyclopentadiene (PCDP) from above was dissolved in 2100 mL of N-methylpyrrolidinone (NMP) in a 5000 mL 3-neck round bottom flask equipped with mechanical stirrer, addition funnel, condenser, thermometer, nitrogen purge and Therm-O-Watch. To this reaction mixture was added 364.6 g (2.389 moles) of vinylbenzylchloride (60/40 para/meta isomer ratio) and 0.6 g of 2,6-di-tert-butyl-p-cresol (BHT). The reaction mixture was heated to 60° C. and 147.4 g (2.627 moles) of potassium hydroxide in 325 mL of methanol was added dropwise over a 2 hour interval. The reaction was maintained at 60° C. for 6 hrs with stirring under a nitrogen purge. To this reaction mixture was added 157.0 g (1.276 moles) of n-propyl-bromide, and then 71.82 g (1.280 moles) of potassium hydroxide in 165 mL of methanol was added over a 2 hour interval. The reaction was maintained at 60° C. for 4 hours and then allowed to cool to room temperature.

The reaction mixture was then transferred to a separatory funnel, and 4.0 Liters of toluene added and then washed thrice with 2.0 Liters of water, dried over sodium sulfate, filtered and concentrated under vacuum, yielding a red resinous product; Mn=740, Mw=1500, dispersity of 2.03.

EXAMPLE 7

Synthesis of Styrene Terminated Para-Cresol Dicyclopentadiene (STPCDP (70VBz/30Pr))

500.0 grams of para-cresol dicyclopentadiene (PCDP) from Borden Chemical (Mn 520, Mw 1100, dispersity of 2.12) and 500 mL of ortho-dichlorobenzene was charged into a 2000 mL 3-neck round bottom flask equipped with mechanical stirrer, addition funnel, condenser, thermometer, Therm-O-Watch, and Nitrogen purge. The reaction mixture was heated to 60° C. under nitrogen with stirring; after complete dissolution of PCDP then 1.0 mL ($6.83 \times 10^{-3}$ moles) of boron trifluoride etherate was added. To this reaction mixture was added 71.12 g (0.538 moles) of dicyclopentadiene over a 45 minute interval, the reaction was maintained at 60° C. with stirring during the addition; then the reaction was heated to 150° C. for 4 hours, and then cooled to ambient temperature. The reaction mixture was coagulated by addition to methanol, filtered, and then dried in a vacuum oven at 80° C. overnight; Mn=700, Mw=1500, dispersity of 2.14.

308.0 grams of the para-cresol dicyclopentadiene (PCDP) from above was dissolved in 1050 mL of N-methylpyrrolidinone (NMP) in a 2000 mL 3-neck round bottom flask equipped with mechanical stirrer, addition funnel, condenser, thermometer, nitrogen purge and Therm-O-Watch. To this reaction mixture was added 189.0 g (1.238 moles) of vinylbenzylchloride (60/40 para/meta isomer ratio) and 0.20 g of 2,6-di-tert-butyl-p-cresol (BHT). The reaction mixture was heated to 60° C. and 76.82 g (1.370 moles) of potassium hydroxide in 225 mL of methanol was added dropwise over a 1.75 hour interval. The reaction was maintained at 60° C. for 4.2 hrs with stirring under a nitrogen purge. To this reaction mixture was added 78.83 g (0.640 moles) of n-propylbromide, and then 35.91 g (0.640 moles) of potassium hydroxide in 125 mL of methanol added over a 2.0 hour interval. The reaction was maintained at 60° C. for 16 hours and then allowed to cool to room temperature. The reaction mixture was then transferred to a separatory funnel, and 3 Liters of toluene added and then washed thrice with 2.0 Liters of water, dried over magnesium sulfate, filtered and concentrated under vacuum, yielding 332.0 g of red resinous product; Mn 670, Mw 1300, dispersity of 1.9.

EXAMPLE 8

Synthesis of Styrene Terminated Para-Cresol Dicyclopentadiene (STPCDP (65VBz/35Pr))

500.0 grams of para-cresol dicyclopentadiene (PCDP) from Borden Chemical (Mn 520, Mw 1100, dispersity of 2.12) and 500 mL of ortho-dichlorobenzene was charged into a 2000 mL 3-neck round bottom flask equipped with mechanical stirrer, addition funnel, condenser, thermometer, Therm-O-Watch, and Nitrogen purge. The reaction mixture was heated to 60° C. under nitrogen with stirring; after complete dissolution of PCDP then 1.0 mL ($6.83 \times 10^{-3}$ moles) of boron trifluoride etherate was added. To this reaction mixture was added 59.26 g (0.448 moles) of dicyclopentadiene over a 2 hour interval, the reaction was maintained at 60° C. with stirring during the addition; then the reaction was heated to 150° C. for 4 hours, and then cooled to ambient temperature. The reaction mixture was coagulated by addition to methanol, filtered, and then dried in a vacuum oven at 80° C. overnight; Mn=630, Mw=1400, dispersity of 2.22.

146.22 grams of the para-cresol dicyclopentadiene (PCDP) from above was dissolved in 600 mL of N-methylpyrrolidinone (NMP) in a 2000 mL 3-neck round bottom flask equipped with mechanical stirrer, addition funnel, condenser, thermometer, nitrogen purge and Therm-O-Watch. To this reaction mixture was added 64.76 g (0.424 moles) of vinylbenzylchloride (60/40 para/meta isomer ratio) and 0.15 g of 2,6-di-tert-butyl-p-cresol (BHT). The reaction mixture was heated to 60° C. and 23.81 g (0.424 moles) of potassium hydroxide in 60 mL of methanol was added dropwise over an 1.2 hour interval. The reaction was maintained at 60° C. for 4.0 hrs with stirring under a nitrogen purge. To this reaction mixture was added 40.14 g (0.326 moles) of n-propylbromide, and then added 18.32 g (0.327 moles) of potassium hydroxide in 40 mL of methanol added over an 1 hour interval. The reaction was maintained at 60° C. for 4 hours and then allowed to cool to room temperature. The reaction mixture was then transferred to a separatory funnel, and 1 Liter of toluene added and then washed thrice with 1 Liter of water, dried over sodium sulfate, filtered and concentrated under vacuum, yielding a red resinous product; Mn=710, Mw=1400, dispersity of 1.97.

EXAMPLE 9

A series of styrene terminated para-cresol dicyclopentadiene (STPCDP) of Examples 6, 7, 8, 4, and 5 corresponding respectively to Samples 1, 2, 3, 4, and 5 were cured via the following cure cycle 2 hrs at 80° C. , 16 hrs. at 100° C. , 4 hrs. at 120° C. , 16 hrs. at 160° C. , 2 hrs. at 200° C. and then 1 hr. at 225° C.. Properties of the cured resins are given in the following table.

TABLE A

| | STPCDP Properties | | | | |
|---|---|---|---|---|---|
| | Sample No. | | | | |
| | 1 | 2 | 3 | 4 | 5 |
| Tg (°C.)$^{(a)}$ | >300 | >300 | >300 | >300 | >300 |
| Tsp (°C.)$^{(b)}$ | 177 ± 8 | 160 ± 5 | 179 ± 6 | 135 ± 5 | 173 ± 7 |
| $\alpha_{sp}$ (ppm/°C.)$^{(c)}$ | 42 ± 2 | 55 ± 9 | 71 ± 6 | 66 ± 10 | 57 ± 5 |
| $\alpha_{260}$ (ppm/°C.)$^{(d)}$ | 96 ± 7 | 85 ± 12 | 155 ± 4 | 125 ± 5 | 86 ± 2 |
| $\epsilon'^{(e)}$ | 2.73 | 2.86 | 2.78 | 2.72 | 2.70 |
| tan $\delta^{(f)}$ | 0.0009 | 0.0001 | 0.001 | 0.0004 | 0.003 |
| $\epsilon'^{(g)}$ | 2.75 | 2.89 | 2.80 | 2.74 | 2.74 |
| tan $\delta^{(h)}$ | 0.004 | 0.004 | 0.005 | 0.002 | 0.002 |
| % Water$^{(i)}$ | 0.145 | 0.156 | 0.161 | 0.089 | 0.107 |

TABLE A-continued

STPCDP Properties

| | Sample No. | | | | |
|---|---|---|---|---|---|
| | 1 | 2 | 3 | 4 | 5 |
| Absorption | | | | | |

[a] glass transition temperature by differential scanning calorimeter
[b] softening point by Thermo Mechanical Analysis - minor thermal transition
[c] coefficient of thermal expansion between 25° C. and softening point
[d] coefficient of thermal expansion between 25° C. and 260° C.
[e] dielectric constant at 1 MHz and 0% Relative Humidity at 25° C.
[f] loss tangent at 1 MHz and 0% Relative Humidity at 25° C.
[g] dielectric constant at 1 MHz and 50% Relative Humidity at 25° C.
[h] loss tangent at 1 MHz and 50% Relative Humidity at 25° C.
[i] at 50% Relative Humidity, 25° C. for 168 hours

EXAMPLE 10

A series of coating solutions were prepared and used to coat silicon surfaces. The solution concentration was 56 wt. % STPCDP from Example 6 in toluene. The solution was applied by spin coating at 950 rpm for 60 seconds. The coated discs were soft baked at 25° C. for 18 hours under vacuum. Then, they were exposed for 3 minutes to UV irradiation with a 300 watt mercury vapor lamp with a quartz/water filter. The irradiated coatings were then exposed to various solvents and the amount of cured resin dissolved was measured. The results are shown in the following tables.

TABLE B

| | % STPCDP[a] Removed Solvent (Toluene:Ethanol)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 2.16 | 2.69 | 0.83 | 0.56 | 0.84 | 0.88 |
| 60 | 4.32 | 2.69 | 2.20 | 0.83 | 2.23 | 0.88 |
| 90 | 3.51 | 2.44 | 2.20 | 0.56 | 2.23 | 1.46 |
| 120 | 3.51 | 3.18 | 1.65 | 1.67 | 0.84 | 1.75 |
| 180 | 3.24 | 2.69 | 0.00 | 2.78 | 0.84 | 1.75 |
| 300 | 5.68 | 4.89 | 1.38 | 1.67 | 0.00 | −0.29 |

[a] STPCDP coated on silicon wafer and soft baked at 25° C. for 18 hrs., 3 minute cure 300 Watt Mercury Vapor Lamp with quartz/water filter.
[b] Weight % solutions.

TABLE C

| | % STPCDP[a] Removed Solvent (Toluene:n-Hexane)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 2.16 | −0.90 | −1.50 | −1.45 | −1.63 | −1.42 |
| 60 | 4.32 | 0.00 | 0.00 | −0.87 | 0.00 | −0.28 |
| 90 | 3.51 | 0.30 | 0.00 | −1.16 | 0.00 | −0.28 |
| 120 | 3.51 | 0.60 | 0.60 | 0.29 | 0.27 | −0.57 |
| 180 | 3.24 | 0.30 | 1.20 | 0.00 | 0.82 | 0.00 |
| 300 | 5.68 | 1.80 | −0.30 | −0.29 | 0.82 | −0.28 |

[a] STPCDP coated on silicon water and soft baked at 25° C. for 18 hrs., 3 minute cure 300 Watt Mercury Vapor Lamp with quartz/water filter.
[b] Weight % solutions.

Tables B and C may be compared with the results of Tables D and E below in which only the soft bake was carried out and no curing by UV radiation was done.

TABLE D

| | % STPCDP[a] Removed Solvent (Toluene:Ethanol)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 97.38 | 97.69 | 90.06 | 15.16 | −4.02 | 0.00 |
| 60 | 101.46 | 100.58 | 100.00 | 41.11 | −0.93 | 0.00 |
| 90 | 102.33 | 100.00 | 100.28 | 57.73 | 0.00 | 2.35 |
| 120 | 102.04 | 100.00 | 99.72 | 63.56 | 1.55 | 1.76 |
| 180 | 101.46 | 100.29 | 100.57 | 69.68 | 2.79 | −0.29 |
| 300 | 100.00 | 100.29 | 100.57 | 74.34 | 0.93 | −0.59 |

[a] STPCDP coated on silicon wafer and soft baked at 25° C. for 18 hrs.
[b] Weight % solutions.

TABLE E

| | % STPCDP[a] Removed Solvent (Toluene:n-Hexane)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 97.38 | 101.71 | −2.82 | −2.82 | −3.42 | −0.58 |
| 60 | 101.46 | 103.43 | 12.43 | 87.32 | 9.97 | −1.17 |
| 90 | 102.33 | 104.29 | 65.54 | 103.38 | 60.40 | −0.58 |
| 120 | 102.04 | 104.00 | 92.66 | 104.23 | 74.36 | 0.58 |
| 180 | 101.46 | 104.00 | 96.33 | 102.82 | 83.19 | −0.58 |
| 300 | 100.00 | 104.29 | 100.56 | 102.82 | 85.75 | −0.58 |

[a] STPCDP coated on silicon water and soft baked at 25° C. for 18 hrs.
[b] Weight % solutions.

EXAMPLE 11

A series of STPCDP solutions were prepared using various concentrations of STPCDP of Example 6 in toluene. These solutions were spin coated onto a silicon substrate (surface) utilizing spin coating rates from 600 rpm to 2000 rpm for 60 seconds; soft baked for 24 hours at 25° C. under vacuum. The samples were then exposed for 3 minutes to UV irradiation with a 300 watt mercury lamp employing an USAF Test Pattern and a quartz/water filter. The photocured polymer was then developed with toluene for 1 minute at 25° C. The air dried substrate was hard baked employing a cure cycle under vacuum of 25° C. to 220° C. ramp in 1 hour, held at 220° C. for 2.5 hours and then cooled to room temperature.

The film thickness of the photocured polymer was analyzed employing a Taylor-Hobson Talysurf 10 profilometer. The following table illustrates the film thicknesses obtained.

TABLE F

| STPCDP Solids Content[a] | Viscosity (mPa s) | Film Thickness (μm) Spin Coating Speed (rpm) | | | | | |
|---|---|---|---|---|---|---|---|
| | | 600 | 700 | 800 | 1000 | 1500 | 2000 |
| 36.7% | 5.0 | — | 4.4 | — | 3.6 | 2.8 | — |
| 50.0% | 15.0 | 8.8 | 8.6 | 7.9 | 7.2 | 6.1 | 5.8 |
| 52.6% | 22.0 | — | 11.3 | — | 9.8 | 8.0 | — |
| 55.6% | 36.0 | — | 17.6 | — | 13.0 | 9.8 | — |

[a] Dissolved solids content in Toluene

EXAMPLE 12

A series of STPCDP solutions were prepared using various concentrations of STPCDP of Example 6 in toluene. These solutions were spin coated onto a silicon substrate (surface) utilizing spin coating rates from 600 rpm to 2000 rpm for 60 seconds; soft baked for 24 hours at 25° C. under vacuum. The samples were then exposed for 3 minutes to UV irradiation with a 300 watt mercury lamp employing an USAF Test Pattern and a quartz/water filter. The photocured polymer was then developed with toluene for 1 minute at 25° C. The air dried substrate was hard baked employing a cure cycle under vacuum of 25° C. to 220° C. ramp in 1 hour, held at 220° C. for 2.5 hours and then cooled to room temperature. The film thickness and sidewall angle of the photocured polymer was analyzed utilizing a Sloan Technology Corporation Dektak 3030 profilometer. This data is summarized in the following table.

TABLE G

| Spin Speed (rpm) | Film Thickness | Sidewall Angle (μm) |
|---|---|---|
| 600 | 10.0 | 31 |
| 600 | 10.0 | 22 |
| 600 | 11.5 | 13 |
| 600 | 12.0 | 28 |
| 700 | 10.8 | 16 |
| 700 | 8.5 | 9 |
| 700 | 9.4 | 39 |
| 700 | 11.3 | 39 |
| 800 | 9.7 | 13 |
| 800 | 7.0 | 5 |
| 800 | 9.0 | 11 |
| 800 | 10.0 | 10 |
| 1000 | 5.9 | 7 |
| 1000 | 9.4 | 12 |
| 1000 | 8.5 | 22 |
| 1000 | 8.3 | 17 |
| 1500 | 6.4 | 24 |
| 1500 | 6.5 | 23 |
| 1500 | 8.0 | 6 |
| 1500 | 7.0 | 20 |
| 2000 | 7.0 | 15 |
| 2000 | 6.8 | 23 |
| 2000 | 6.2 | 24 |

EXAMPLE 13

A series of STPCDP solutions were prepared using various concentrations of STPCDP of Example 6 in toluene. These solutions were spin coated onto a silicon substrate (surface) utilizing spin coating rates from 600 rpm to 2000 rpm for 60 seconds; soft baked for 24 hours at 25° C. under vacuum. The samples were then exposed for 3 minutes to UV irradiation with a 300 watt mercury lamp employing an USAF Test Pattern and a quartz/water filter. The photocured polymer was then developed with toluene for 1 minute at 25° C. The air dried substrate was hard baked employing a cure cycle under vacuum of 25° C. to 220° C. ramp in 1 hour, held at 220° C. for 2.5 hours and then cooled to room temperature The samples were then metallized via ion-beam sputtering to yield a metal film of thickness 5000 to 10000 Å.

The adhesion was evaluated via a calibrated "Scotch-Tape" adhesion test before and after thermal shock cycling. A thermal shock cycle encompasses the following thermal cycling of the sample: hold at −55° C. for 10 minutes, −55° C. to 125° C. over a rapid ramp, hold at 125° C. for 10 minutes. In the following tables the ratio given means that of 25 squares of the metal, some to all of them were not removed by the tape. That is, 25/25 means that all the squares remained adhered to the dielectric polymer while 5/25 means that 20 squares of metal were removed.

| Metal Layer | Adhesion Measurement Results | | | | | |
|---|---|---|---|---|---|---|
| | Before Thermal Shock Cycling | | After 92 Cycles | | After 184 Cycles | |
| | 2.5 lb.(b) | 10.0 lb. | 2.5 lb. | 10.0 lb. | 2.5 lb. | 10.0 lb. |
| Chromium | 8/25 Passed | 8/8 Passed | 8/8 Passed | 8/8 Passed | 7/8 Passed | 6/7 Passed |
| Chromium | 0/25 Passed | — | — | — | — | — |
| Copper | 0/25 Passed | — | — | — | — | — |
| Copper | 0/25 Passed | — | — | — | — | — |
| Aluminum | 25/25 Passed | 25/25 Passed | 25/25 Passed | 25/25 Passed | (a) | (a) |
| Aluminum | 0/25 Passed | — | — | — | — | — |
| Gold | 0/25 Passed | — | — | — | — | — |
| Gold | 0/25 Passed | — | — | — | — | — |
| Nickel | 0/25 Passed | — | — | — | — | — |
| Nickel | 0/25 Passed | — | — | — | — | — |

(a) Sample not evaluated.
(b)Tape rating in lb. for ¼ inch wide tape.

EXAMPLE 14

STPCDP resin of Example 5 was dissolved in toluene to yield a solution of composition 47.2% STPCDP and 52.8% toluene. This solution was spin coated onto an alumina or silicon substrate (surface) utilizing spin coating rate of 1000 rpm for 60 seconds; soft baked for 1 hour at 60° C. under nitrogen. The polymer was hard baked employing a cure cycle under nitrogen of 25° C. to 220° C. ramp in 3 hour, held at 220° C. for 2.0 hours and then ramped from 220° C. to 25° C. in 4 hours.

The adhesion was evaluated via a calibrated "Scotch-Tape" adhesion test before and after thermal shock cycling. A thermal shock cycle encompasses the following thermal cycling of the sample: hold at −55° C. for 10 minutes, −55° C. to 125° C. over a rapid ramp, hold at 125° C. for 10 minutes

| Substrate | Adhesion Measurements Results | | | |
|---|---|---|---|---|
| | Before Thermal Shock Cycling | | After 92 Cycles | |
| | 2.5 lb. | 10.0 lb. | 2.5 lb. | 10.0 lb. |
| Alumina | 25/25 Passed | 25/25 Passed | 25/25 Passed | 25/25 Passed |
| Silicon | 25/25 Passed | 25/25 Passed | 25/25 Passed | 25/25 Passed |

EXAMPLE 15

STPCDP resin of Example 5 was dissolved in toluene to yield a solution of composition 47.2% STPCDP and 52.8% toluene. This solution was spin coated onto an alumina substrate (surface) onto which had been ion-sputtered with a metal film of thickness 5000Å, utilizing spin coating rate of 1000 rpm for 60 seconds; soft baked for 1 hour at 60° C. under nitrogen. The polymer was hard baked employing a cure cycle under nitrogen of 25° C. to 220° C. ramp in 3 hours, held at 220° C. for 2.0 hours and then ramped from 220° C. to 25° C. in 4 hours.

The adhesion was evaluated via a calibrated "Scotch-Tape" adhesion test before and after thermal shock cycling. A thermal shock cycle encompasses the following thermal cycling of the sample: hold at −55° C. for 10 minutes, −55° C. to 125° C. over a rapid ramp, hold at 125° C. for 10 minutes.

| | Adhesion Measurements Results | | | |
|---|---|---|---|---|
| | Before Thermal Shock Cycling | | After 92 Cycles | |
| Metal Layer | 2.5 lb. | 10.0 lb. | 2.5 lb. | 10.0 lb. |
| Chromium | 25/25 Passed | 25/25 Passed | 25/25 Passed | 25/25 Passed |
| Nickel | 25/25 Passed | 25/25 Passed | 25/25 Passed | 25/25 Passed |
| Copper | 25/25 Passed | 25/25 Passed | 25/25 Passed | 25/25 Passed |
| Aluminum | 25/25 Passed | 25/25 Passed | (a) | (a) |
| Gold | 25/25 Passed | 25/25 Passed | 25/25 Passed | 25/25 Passed |

(a) Sample not evaluated.

It can be seen in the above Examples 13-15 that chromium adhered particularly well to the dielectric polymers and thus can serve as a suitable base for copper layers which provide conductive patterns in the multilevel structures.

We claim:

1. A method of forming a polymer on a substrate in a predetermined pattern comprising:
   (a) coating a substrate with a prepolymer which is an ether of the reaction product of dicyclopentadiene with phenol having the formula

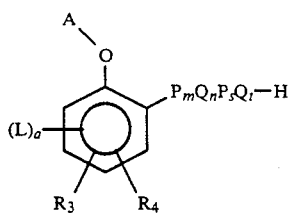

where P =

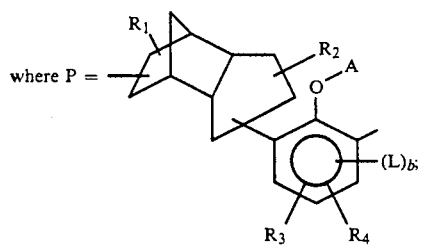

-continued

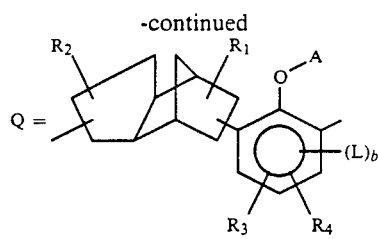

with
$R_1$, $R_2$=H or alkyl of 1-10 carbon atoms;
$R_3$=methyl;
$R_4$=H;
A=H

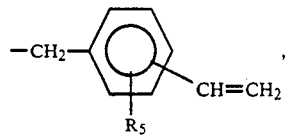

an alkyl moiety containing 1 to 10 carbon atoms, a cycloalkyl moiety having 5 to 10 carbon atoms, or benzyl, subject to the constraint that at least 50% of all A's are the vinyl benzyl moiety;
L=Br or Cl;
a=0, 1, or 2;
b=0 or 1;
m, n, s, and t are 0 or an integer, and $m+n+s+t=z$ is an integer from 1-10; and
$R_5$=H, an alkyl moiety of 1-10 carbon atoms, a halogen or alkoxy moiety, or a monovalent aromatic radical.
   (b) irradiating the coated prepolymer of (a) through a masking pattern to selectively crosslink the portion of said coating being irradiated;
   (c) selectively dissolving the non-irradiated part of the prepolymer coating of (a); and
   (d) curing the crosslinked portion of the prepolymer coating by heating at a temperature in the range of 100° C. to 300° C. for a time sufficient to further crosslink said crosslinked coating and to transform the prepolymer to an infusible glassy solid.

2. The method of claim 1 wherein $R_1$ and $R_2$ are hydrogen.

3. The method of claim 1 wherein Z is 3 or 4.

4. The method of claim 1 wherein A is para vinyl benzyl.

5. The method of claim 1 wherein L is Br.

6. The method of claim 1 wherein 70% of A is vinyl benzyl and the remainder is propyl.

7. The method of claim 1 wherein the coating of (a) is softbaked before the irradiation of (b).

8. The method of claim 1 wherein the coating of (a) includes a photosensitizer of photoinitiator.

9. The method of claim 1 wherein the irradiation of (b) has a wavelength of 200 to 500 nm.

10. An electronic interconnect structure prepared by the method of claim 1.

11. An electronic interconnect structure of claim 10 wherein said structure polymer is adhered to a layer of chromium metal.

* * * * *

UNITED STATES PATENT AND TRADEMARK OFFICE
CERTIFICATE OF CORRECTION

PATENT NO. : 5,085,886

Page 1 of 2

DATED : February 4, 1992

INVENTOR(S) : Zupancic et al.

It is certified that error appears in the above-identified patent and that said Letters Patent is hereby corrected as shown below:

Column 2, line 26: after "A=H" insert --,--
         line 33: after "CH=CH$_2$" insert --,--
Column 3, line 33: after "A=H" insert --,--
         line 38: after "CH=CH$_2$" insert --,--
         line 67: delete "C"
         line 68: "eondensation" should read --condensation--
Column 4, line 12: "is 1 or 2" should read --is 0, 1 or 2--
Column 5, line 65: "there" should read --these--
Column 8, line 18: after "it" insert --.--
Column 9, line 49: "1.32 g" should read --31.32 g--
Column 10, line 8: after "interval" insert --.--
Column 11, line 34: "reaction mixture Was" should read
                  --reaction mixture was--

UNITED STATES PATENT AND TRADEMARK OFFICE
CERTIFICATE OF CORRECTION

PATENT NO. : 5,085,886
DATED : February 4, 1992
INVENTOR(S) : Zupancic et al.

It is certified that error appears in the above-identified patent and that said Letters Patent is hereby corrected as shown below:

Column 12, line 16: "02.0 g" should read --102.0 g--
Column 13, line 47: after "perature" insert --.--
Column 17, line 58: after "perature" insert --.--
Column 20, line 57: "of photoinitiator" should read --or photoinitiator--
          line 63: "polymer" should be deleted Signed and Sealed this Fifteenth Day of June, 1993

Attest:

MICHAEL K. KIRK

Attesting Officer
Acting Commissioner of Patents and Trademarks